United States Patent [19]
Kim et al.

[11] Patent Number: 6,063,778
[45] Date of Patent: May 16, 2000

[54] CEPHALOSPORIN DERIVATIVES AND PROCESSES FOR THE PREPARATION THEREOF

[75] Inventors: Kee-Won Kim; Jae-Hoon Kang, both of Seoul; Dong-Sik Yu, Kyungki-do; Moo-Soo Jang, Kyungki-do; Seung-Woo Yu, Kyungki-do, all of Rep. of Korea

[73] Assignee: Il-Dong Pharm. Co., Ltd., Seoul, Rep. of Korea

[21] Appl. No.: 09/091,883

[22] PCT Filed: Dec. 27, 1996

[86] PCT No.: PCT/KR96/00255

§ 371 Date: Jun. 26, 1998

§ 102(e) Date: Jun. 26, 1998

[87] PCT Pub. No.: WO97/24359

PCT Pub. Date: Jul. 10, 1997

[30] Foreign Application Priority Data

Dec. 28, 1995 [KR] Rep. of Korea ...................... 95-61498

[51] Int. Cl.⁷ ...................... A61K 31/546; C07D 501/24
[52] U.S. Cl. .......................... 514/202; 514/206; 540/222; 540/226; 540/227
[58] Field of Search .................................... 540/222, 227, 540/226; 514/202, 206

[56] References Cited

U.S. PATENT DOCUMENTS

| | | | |
|---|---|---|---|
| 3,658,649 | 4/1972 | Arnold et al. | 260/243 C |
| 4,079,180 | 3/1978 | Suzuki et al. | 544/30 |
| 5,373,000 | 12/1994 | Machida | 514/202 |
| 5,424,196 | 6/1995 | Cambiaghi et al. | 435/51 |

FOREIGN PATENT DOCUMENTS

0333154A2  9/1989  European Pat. Off. .

OTHER PUBLICATIONS

I. Csendes, B.W. Müller and W. Tosch, "The Journal of Antibiotics" vol. 36, p. 1020 Cephalosporin Antibiotics. Synthesis and Antimicrobial activity of 7β-[2-(5-Amino-1, 2,4-Thiadiazol-3-YL)-2-Oxyiminoacetamido]Cephalosporin Derivatives (Aug. 1983).

Hajime Kamachi, Masahisa Oka, Yukio Narita, Seiji Iimura, Shimpei Aburaki, Haruhiro Yamashita, Kozo Tomatsu, Jun Okumura and Takayuki Naito, "The Journal of Antibiotics" vol. 43, p. 533 Synthesis of a New Series of Cephalosporins Having 3-Substituted-Ammonio-1-Propenyl Group as the C-3 Side Chain May 1990.

Akio Miyake, Yoshinobu Yoshimura, Masayoshi Yamaoka, Tatsuo Nishimura, Naoto Hashimoto and Akira Imada, "The Journal Of Antibiotics" 45, p. 709 Studies on Condensed-Heterocyclic Azolium Cephalosporins, IV. Synthesis and Antibacterial Activity of 7β-[2-(5-Amino-1,2, 4-Thiadiazol-3-YL)-Alkoxyiminoacetamido]-3-(Condensed-Heterocyclic Azolium)Methyl Cephalosporins Including SCE-2787.

*Primary Examiner*—Mark L. Berch
*Attorney, Agent, or Firm*—Birch, Stewart, Kolasch & Birch, LLP

[57] ABSTRACT

The invention provides novel cephalosporin derivatives of the formula (I)

(I)

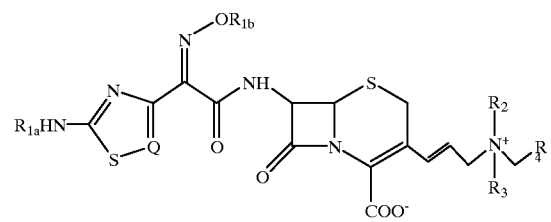

and salts thereof for use in pharmaceutical compositions. Also novel precursors for synthesis of the cephalosporins are disclosed.

4 Claims, No Drawings

CEPHALOSPORIN DERIVATIVES AND PROCESSES FOR THE PREPARATION THEREOF

This application is the national phase under 35 U.S.C. §371 of prior PCT International Application No. PCT/KR96/00255 which has an international filing date of Dec. 27, 1996 which designated the United States of America, the entire contents of which are hereby incorporated by reference.

FIELD OF THE INVENTION

The present invention relates to novel cephalosporin derivatives of the formula(I) and pharmaceutically acceptable non-toxic salts thereof; and more particularly, to processes for preparing these compounds and to pharmaceutical compositions containing the same as active ingredients, which have broad antibacterial activities against both Gram-positive and Gram-negative bacteria.

SUMMARY OF THE INVENTION

An object of the present invention is to provide the novel cephalosporin derivatives of the formula(I) and pharmaceutically acceptable non-toxic salts thereof.

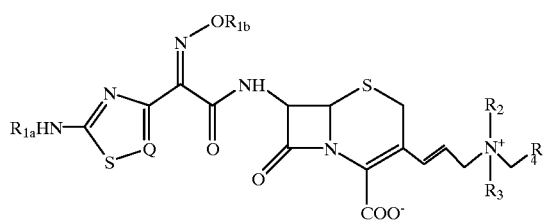

(I)

wherein $R_{1a}$ is a hydrogen atom or an amino protecting group;

$R_{1b}$ is a hydrogen atom, $C_{1-4}$ alkyl group, $C_{2-4}$ alkenyl group, $C_{2-4}$ alkynyl group, fluoro-substituted $C_{1-3}$ alkyl group or a substituted or unsubstituted carboxyalkyl group (preferably methyl group, ethyl group, allyl group, propargyl group, fluoromethyl group, 2-fluoroethyl group, —C(CH$_3$)$_2$COOH group, —CH$_2$COOH group);

Q is CH or N;

$R_2$ and $R_3$ may be the same or different and mean individually a group selected from $C_{1-3}$ alkyl group, $C_{2-4}$ alkenyl group, $C_{2-4}$ alkynyl group and hydroxyl-substituted $C_{1-3}$ alkyl group; and $R_4$ is

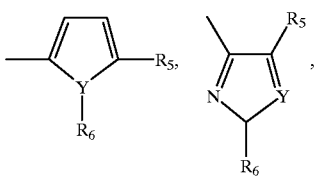

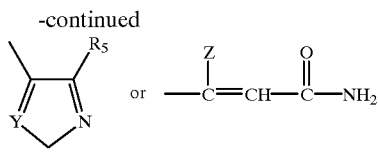

wherein $R_5$ is a hydrogen atom, $C_{1-3}$ alkyl group or a hydroxyl-substituted $C_{1-3}$ alkyl group;

$R_6$ is a hydrogen atom, $C_{1-3}$ alkyl group, $C_{2-4}$ alkenyl group or an amino group;

$R_7$ is a $C_{1-3}$ alkyl group or a hydroxyl-substituted $C_{1-3}$ alkyl group;

Y is O or S or N; and

Z is a hydrogen atom, $C_{1-3}$ alkyl group, chlorine or fluorine atom.

DETAILED DESCRIPTION OF THE INVENTION

The cephalosporin compounds of the formula(I) can be prepared by the displacement reaction of the compounds of the formula(III) with the compounds of the formula(IV).

The compounds of the formula(III) can be prepared in accordance with known methods(J. of. Antibiotics., 43, 5, 533, 1990. European Patent No. 0333154).

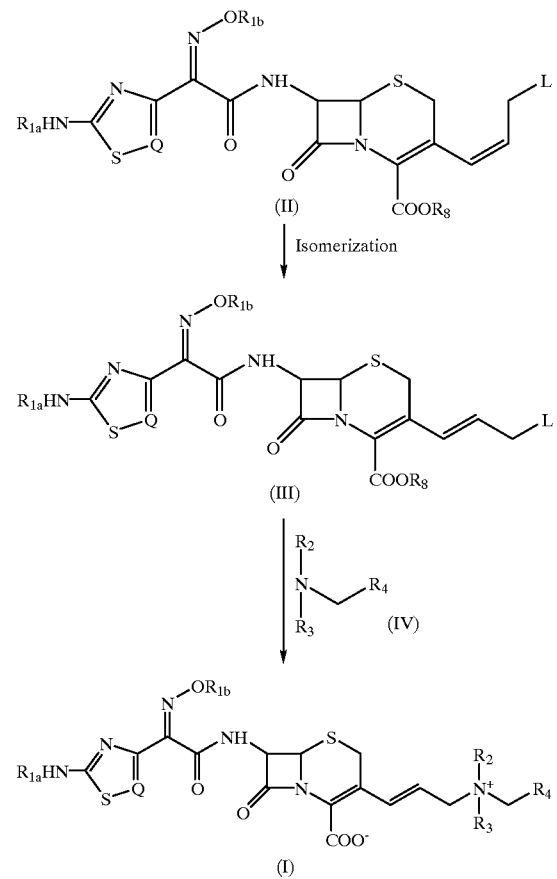

wherein $R_{1a}$, $R_{1b}$, $R_2$, $R_3$, $R_4$ and Q are the same as defined above;

$R_8$ is a hydrogen atom or a carboxyl protecting group; and

L is a leaving group.

Also, the cephalosporin compounds of the formula(I) can be prepared by the acylation reaction of the compounds of the formula(VIII) with the activated form of the compounds of the formula(IX).

The compounds of the formula(IX) can be prepared in accordance with known methods (J. of. Antibiotics., 36, 8, 1020, 1983. J. of. Antibiotics., 45, 5, 709, 1992).

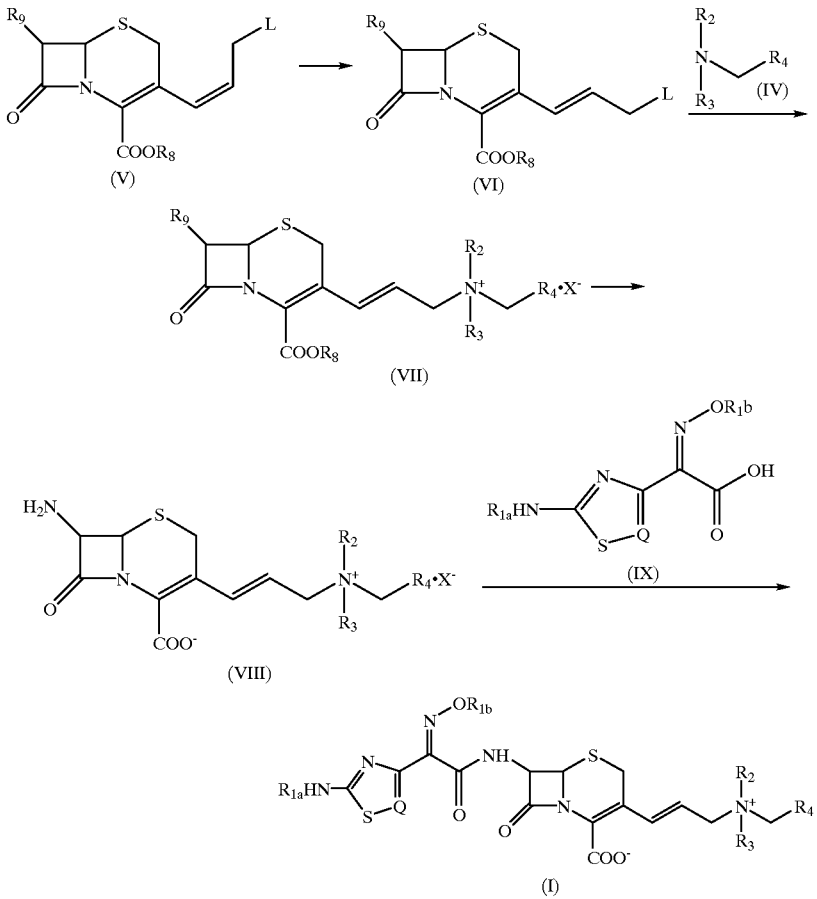

wherein $R_{1a}$, $R_{1b}$, $R_2$, $R_3$, $R_4$ $R_8$, Q and L are the same as defined above;

$R_9$ is ani acyl group, formyl group, salicylaldehyde group or benzaldehyde group; and X is a halogen atom or an acid residue.

Specific examples of the compounds of formula(I) provided by this invention are shown below:

7β-[(Z)-2-(2-aminothiazol-4-yl)-2-methoxyiminoacetamido]-3-[(E)-3-[(4-methylthiazol-5-yl)-methyldimethylammonio]-1-propen-1-yl]3-cephem-4-carboxylate or pharmaceutically acceptable non-toxic salts thereof.

7β-[(Z)-2-(2-aminothiazol-4-yl)-2-methoxyiminoacetamido]-3-[(E)-3-[(1-carbamoyl-1-propen-3-yl)-3-ethylmethylammonio]-1-propen-1-yl]3-cephem-4-carboxylate or pharmaceutically acceptable non-toxic salts thereof.

7β-[(Z)-2-(2-aminothiazol-4-yl)-2-fluoroethoxyiminoacetamido]-3-[(E)-3-[(4-methylthiazol-5-yl)-methyldimethylammonio]-1-propen-1-yl]3-cephem-4-carboxylate or pharmaceutically acceptable non-toxic salts thereof.

7β-[(Z)-2-(2-aminothiazol-4-yl)-2-fluoroethoxyiminoacetamido]-3-[(E)-3-[(1-carbamoyl-1-propen-3-yl)-3-ethylmethylammonio]-1-propen-1-yl]3-cephem-4-carboxylate or pharmaceutically acceptable non-toxic salts thereof.

7β-[(Z)-2-(5-amnino-1,2,4-thiadiazol-3-yl)-2-methoxyiminoacetamido]-3-[(E)-3-[(1-carbamoyl-1-propen-3-yl)-3-ethylmethylammonio]-1-propen-1-yl]3-cephem-4-carboxylate or pharmaceutically acceptable non-toxic salts thereof.

7β-[(Z)-2-(5-amnino-1,2,4-thiadiazol-3-yl)-2-methoxyiminoacetamido]-3-[(E)-3-[(4-methylthiazol-5-yl)-methyldimethylammonio]-1-propen-1-yl]-cephem-4-carboxylate or pharmaceutically acceptable non-toxic salts thereof.

7β-[(Z)-2-(5-amino-1,2,4-thiadiazol-3-yl)-2-fluoroethoxyiminoacetamido]-3-[(E)-3-[(4-methylthiazol-5-yl)-methyldimethylammonio]-1-propen-1-yl]3-cephem-4-carboxylate or pharmaceutically acceptable non-toxic salts thereof.

7β-[(Z)-2-(5-amino-1,2,4-thiadiazol-3-yl)-2-fluoroethoxyiminoacetamido]-3-[(E)-3-[(1-carbamoyl-1-propen-3-yl)-3-ethylmethylammonio]-1-propen-1-yl]3-cephem-4-carboxylate or pharmaceutically acceptable non-toxic salts thereof.

The following preparations and examples are provided for the purpose of illustrating certain aspects of the present invention only; and are not to be construed as limiting the scope of the present invention in any way.

Preparation 1
Preparation of 5-dimethylaminomethyl-4-methyloxazole a) Preparation of 4-methyl-5-oxazolecarboxylic acid ethyl ester To ethyl-2-chloroacetoacetate(5.6 g) was added formamide(4.6 g). The reaction mixture was stirred at 120° C. for 12 hours, cooled to 0° C. and aqueous potassium carbonate was added thereto. The mixture was extracted with benzene, dried with anhydrous magnesium sulfate, and concentrated in vacuo to obtain the target product(2.1 g).

NMR(CDCl$_3$) δ (ppm): 1.40(t,3H), 2.50(s,3H), 4.35(q, 2H), 7.84(s,1H).

b) Preparation of 5-hydroxymethyl-4-methyloxazole

After 4-methyl-5-oxazolecarboxylic acid ethyl ester(3 g) was dissolved in ethyl alcohol(50 ml), sodiumborohydride(3 g) was added thereto and refluxed for 17 hours. The reaction mixture was concentrated under reduced pressure, water was added to the concentrated solution. After extraction with ethyl acetate dried with anhydrous magnesium sulfate, and then concentrated to obtain the target product(0.9 g).

NMR(CDCl$_3$) δ (ppm): 2.18(s,3H), 3.45(s,1H), 4.65(s, 2H), 7.80(s,1H).

c) Preparation of 5-dimethylaminomethyl-4-methyloxazole

To a solution of 5-hydroxymethyl-4-methyloxazole(2 g) dissolved in dichloromethane(20 ml) were added thionylchloride(3.9 ml) at 0° C. After stirring at room temperature for 4 hours, ice-water(15 ml) were added thereto. The seperated organic layer was dehydrated and concentrated. The residue were added ethylalcohol(25 ml) dimethylamine hydrochloride (2.5 g) and potassium carbonate(6.3 g). After stirring at room temperature for 4 hours, the solid was filtered off. The filtrate was concentrated under reduced pressure, water and dichloromethane added thereto. The separated organic layer was dehydrated, and concentrated to obtain the target product(0.9 g).

NMR(CDCl$_3$) δ (ppm): 2.12(s,3H), 2.24(s,6H), 3.42(s, 2H), 7.78(s,1H).

Preparation 2
Preparation of 5-dimethylaminomethyl-4-methylthiazole a) Preparation of 4-methyl-5-thiazolecarboaldehyde.

To a solution of pyridinium dicromate(164.19 g) in dichloromethane (600 ml), water(20 ml) was added. A solution of 4-methyl-5-thiazoleethanol(10 g) in dichloromethane(500 ml) was added dropwise to the mixture and the resulting mixture stirred at room temperature for 24 hours. The solid was filtered off and washed with water. The separated organic layer was dehydrated, and concentrated to obtain the target product(6 g).

NMR(CDCl$_3$) δ (ppm): 2.79(s,3H), 9.02(s,1H), 10.18(s, 1H).

b) Preparation of 4-methyl-5-thiazolemethanol

To sodiumborohydride(2.32 g) was added tetrahydrofurane(35 ml)at 0° C. A solution of 4-methyl-5-thiazolecarboaldehyde(6 g) in tetrahydrofurane (35 ml) was added dropwise to the mixture and the resulting mixture stirred at room temperature for 3 hours. To the reaction mixture was added ice-water(60 ml) and saturated brine(30 ml). The separated organic layer was dehydrated, and concentrated to obtain the target product(5 g).

NMR(CDCl$_3$) δ (ppm): 2.35(s,3H), 4.79(s,2H), 8.61(s, 1H).

c) Preparation of 5-dimethylaminomethyl-4-methylthiazole

To a solution of 4-methyl-5-thiazolemethanol(1.5 g) in chloroform(50 ml), thionylchloride (1.7 ml) was added, and the mixture was refluxed for 2 hours. The reaction mixture was concentrated under reduced pressure. The residue were added ethylalcohol(25 ml), dimethylamine hydrochloride (1.33 g) and potassium carbonate(2.3 g). After refluxing for 5 hours, the solid was filtered off. The filtrate was concentrated under reduced pressure, water and chloroform added thereto. The separated organic layer was dehydrated, and concentrated to obtain the target product(1 g).

NMR(CDCl$_3$) δ (ppm): 2.24(s,6H), 2.41(s,3H), 3.63(s, 2H), 8,62(s,1H).

Preparation 3
Preparation of 4-ethylmethylamino-2-butenylamide a) Preparation of 4-bromo-2-butenenitrile To a solution of allylcyanide(40 g) dissolved in tert-butanol(60 ml) and petroleum ether(273 ml) was added bromine(30.6 ml) dissolved in tert-butanol(60.8 ml) at 15° C., and then stirred at room temperature for 15~30 minutes. To sodium ethoxide(222.6 ml, 21%) was added dropwise to the mixture and the solid was filtered off. The filtrate was distilled under reduced pressure to obtain the target product (55 g) b.p: 80~85° C.(12 mm).

NMR(CDCl$_3$) δ (ppm): 4.10(s,2H), 5.54(m,1H), 6.81(m, 1H).

b) Preparation of 4-bromo-2-butenylamide

To a solution of 4-bromo-2-butenenitrile(20 g) suspended in water (2.3 ml) was added slowly sulfuric acid(7.8 ml) at 40° C., and then stirred at 80~90° C. for an hour. The reaction mixture was cooled to 40° C., and then added ice(40 g) and ammonia solution(19.8 ml). The resulting precipitate was collected by filtration and recrystallized from ethylacetate to obtain the target product(7.7 g).

NMR(CDCl$_3$) δ (ppm): 4.15(d,2H), 5.8~6.2(br m,1H, NH$_2$), 6.92(m,1H).

c) Preparation of 4-ethylmethylamino-2-butenylamide

To a solution of 4-bromo-2-butenylamide(5.4 g) in acetonitrile(55 ml), N-ethylmethylamine(5.7 ml) was added at 0° C. The reaction mixture was stirred for an hour and the resulting precipitate was collected by filtration to obtain the target product(3.1 g).

NMR(DMSO-d$_6$) δ (ppm): 1.01(t,2H), 2.13(s,3H), 2.35 (q,2H), 3.04(d,2H), 5.99(d,1H), 6.55(m,1H).

EXAMPLE 1

Synthesis of 7β-[(Z)-2-(2-aminothiazol-4-yl)-2-methoxyiminoacetamido]-3-[(E)-3-[(4-methylthiazol-5-yl)-methyldimethylammonio]-1-propen-1-yl]3-cephem-4-carboxylate To a solution of p-methoxybenzyl 7β-[(Z)-2-methoxyimino-2-(2-tritylaminothiazol-4-yl)acetamido]-3-[(Z)-3-chloro-1-propen-1-yl]3-cephem-4-carboxylate(1.5 g) dissolved in acetone(30 ml), sodium iodide(0.82 g) was added thereto under ice-cooling. The resulting solution was stirred for 15 minutes under ice-cooling and for additional 60 minutes at room temperature. The solvent was distilled off, and the residue was extracted with ethyl acetate. The extract was washed with a 10%-sodium thiosulfate and with a saturated brine, followed by drying with addition of anhydrous magnesium sulfate. The dried extract was concentrated under reduced pressure and the resulting precipitates were collected by filtration to obtain 1.2 g of p-methoxybenzyl 7β-[(Z)-2-methoxyimino-2-(2-tritylaminothiazol-4-yl)acetamido]-3-[(E)-3-iodo-1-propen-1-yl]3-cephem-4-carboxylate. The powder was dissolved in N,N-dimethylformamide(2 ml), and 5-dimethylaminomethyl-4-methylthiazole(0.31 g) was added thereto at −10° C. The resulting solution was stirred for 4 hours at −10° C. 10%-sodium thiosulfate(70 ml) was added to the reaction solution, and the resulting precipitates were collected by filtration to obtain the yellowish brown powder. The powder was stirred in 88% formic acid(1.8 ml) for an hour at 40° C., and acetone(400 ml) was added thereto. The resulting precipitates were collected by filtration and washed with acetone. The precipitates were chromatographed over silicagel [acetonitrile:distilled water 4:1 (v/v)], Sephadex LH-20(or Amberlite XAD-2), and then lyophilized to obtain the target product (250 mg) as white solid.

mp: 181° C.(dec.); IR(KBr,cm$^{-1}$): 1762, 1663, 1608, 1530; NMR(DMSO-d$_6$) δ (ppm): 2.43(s,3H), 2.94(s,6H), 3.42(s,2H), 3.82(s,3H), 4.01(d,2H), 4.62(s,2H), 5.04(d,1H), 5.58(d,1H), 5.62(br d,1H), 7.1~7.4(d,1H. s,1H. s,1H), 9.62 (d,1H)

EXAMPLE 2

Synthesis of 7β-[(Z)-2-(2-aminothiazol-4-yl)-2-methoxyiminoacetamido]-3-[(E)-3-[(5-methylimidazol-4-yl)-methyldimethylammonio]-1-propen-1-yl]3-cephem-4-carboxylate The same procedures as described in Example 1 were repeated using 0.17 g of 4-dimethylaminomethyl-5-methylimidazole in place of 5-dimethylaminomethyl-4-methylthiazole to obtain the target product(100 mg).

mp: 178° C.(dec.); IR(KBr,cm$^{-1}$): 1760, 1670, 1610, 1531; NMR(DMSO-d$_6$) δ (ppm): 2.25(s,3H), 2.98(s,6H), 3.38(s,2H), 3.80(s,3H), 4.11(d,2H), 4.59(s,2H), 5.01(d,1H), 5.53(d,1H), 5.59(br d,1H), 7.2~7.84(d,1H. s,1H. s,1H), 9.66 (d,1H).

EXAMPLE 3

Synthesis of 7β-[(Z)-2-(2-aminothiazol-4-yl)-2-methoxyiminoacetamido]-3-[(E)-3-[(2-aminothiazol-4-yl)-methyldimethylammonio]-1-propen-1-yl]-3-cephem-4-carboxylate The same procedures as described in Example 1 were repeated using 0.21 g of 4-dimethylaminomethyl-2-aminothiazole in place of 5-dimethylaminomethyl-4-methylthiazole to obtain the target product(150 mg).

mp: 192° C.(dec.); IR(KBr,cm$^{-1}$): 1760, 1672, 1600, 1530; NMR(DMSO-d$_6$) δ (ppm): 2.12(s,6H), 3.35(s,2H), 3.83(s,3H), 4.01(d,2H), 4.55(s,2H), 5.02(d,1H), 5.58(d,1H), 5.62(br d,1H), 6.72(br,2H), 7.1~7.5(d,1H. s,1H. s,1H), 9.60 (d,1H).

EXAMPLE 4

Synthesis of 7β-[(Z)-2-(2-aminothiazol-4-yl)-2-methoxyiminoacetamido]-3-[(E)-3-[(thiopen-2-yl)-methyldimethylammonio]-1-propen-1-yl]3-cephem-4-carboxylate The same procedures as described in Example 1 were repeated using 0.18 g of 2-thiopenmethyldimethylamine in place of 5-dimethylaminomethyl-4-methylthiazole to obtain the target product (170 mg).

mp: 186° C.(dec.); IR(KBr,cm$^{-1}$): 1762, 1670, 1600, 1530; NMR(DMSO-d$_6$) δ (ppm): 2.98(s,6H), 3.32(s,2H), 3.88(s,3H), 4.01(d,2H), 4.49(s,2H), 5.02(d,1H), 5.55(d,1H), 5.62(br d,1H), 6.70(br d,2H. 1H), 7.1~7.7(d,1H. s,1H. s,1H), 9.60(d,1H).

EXAMPLE 5

Synthesis of 7β-[(Z)-2-(2-aminothiazol-4-yl)-2-methoxyiminoacetamido]-3-[(E)-3-[(4-methyloxazol-5-yl)-methyldimethylammonio]-1-propen-1-yl]3-cephem-4-carboxylate The same procedures as described in Example 1 were repeated using 0.31 g of 5-dimethylaminomethyl-4-methyloxazole in place of 5-dimethylaminomethyl-4-methylthiazole to obtain the target product (300 mg).

mp: 199° C.(dec.); IR(KBr,cm$^{-1}$): 1762, 1668, 1610, 1533; NMR(DMSO-d$_6$) δ (ppm): 2.25(s,2H), 2.95(s,6H), 3.42(s,2H), 3.84(s,1H), 4.01(d,2H), 4.62(s,2H), 5.04(d,1H), 5.58(d,1H), 5.62(br d,1H), 7.1~7.3(d,1H. s,1lH. s,1H), 9.58 (d,1H).

EXAMPLE 6

Synthesis of 7β-[(Z)-2-(2-aminothiazol-4-yl)-2-methoxyiminoacetamido]-3-[(E)-3-[(1-carbamoyl-1-propen-3-yl)-3-ethylmethylammonio]-1-propen-1-yl] 3-cephem-4-carboxylate The same procedures as described in Example 1 were repeated using 0.23 g of 4-ethylmethylamino-2-butenylamide in place of 5-dimethylaminomethyl-4-methylthiazole to obtain the target product (190 mg).

mp: 189° C.(dec.); IR(KBr,cm$^{-1}$): 1761, 1675, 1608, 1530; NMR(DMSO-d$_6$) δ (ppm): 1.29(t,3H), 2.98(s,3H), 3.82(s,3H), 3.85(q,2H), 3.90(d,2H), 3.94(d,2H), 4.75(s,2H), 5.08(d,1H), 5.62(d,1H), 5.68(br d,1H), 6.75(d,1H), 6.99–7.12(br d,1H), 7.21~7.38(d,1H. s,1H), 9.59(d,1H).

EXAMPLE 7

Synthesis of 7β-[(Z)-2-(2-aminothiazol-4-yl)-2-methoxyiminoacetamido]-3-[(E)-3-[(1-carbamoyl-1-propen-3-yl)-3-dimethylammonio]-1-propen-1-yl]3-cephem-4-carboxylate The same procedures as described in Example 1 were repeated using 0.25 g of 4-dimethylamino-2-butenylamide in place of 5-dimethylaminomethyl-4-methylthiazole to obtain the target product(200 mg).

mp: 198° C.(dec.); IR(KBr,cm$^{-1}$): 1763, 1670, 1600, 1530; NMR(DMSO-d$_6$) δ (ppm): 3.11(s,6H), 3.88(s,3H), 3.92(d,2H), 3.95(d,2H), 4.07(s,2H), 5.05(d,1H), 5.62(d,1H), 5.69(br d,1H), 6.73(d,1H), 7.01–7.14(br d,1H), 7.18~7.32 (d,1H. s,1H), 9.57(d,1H).

EXAMPLE 8

Synthesis of 7β-[(Z)-2-(2-aminothiazol-4-yl)-2-methoxyiminoacetamido]-3-[(E)-3-[(4-methylthiazol-5-yl)-methylethylmethylammonio]-1-propen-1-yl]3-cephem-4-carboxylate The same procedures as described in Example 1 were repeated using 0.35 g of 5-ethylmethylaminomethyl-4-methylthiazole in place of 5-dimethylaminomethyl-4-methylthiazole to obtain the target product (300 mg).

mp: 194° C.(dec.); IR(KBr,cm$^{-1}$): 1762, 1662, 1610, 1530; NMR(DMSO-d6) δ (ppm): 1.33(t,3H), 2.44(s,3H), 2.92(s,3H), 3.43(s,2H), 3.85(q,2H), 3.87(s,3H), 4.01(d,2H), 4.60(s,2H), 5.05(d,1H), 5.56(d,1H), 5.67(br d,1H), 7.18~7.32(d,1H. s,1H. s,1H), 9.60(d,1H).

EXAMPLE 9

Synthesis of 7β-[(Z)-2-(2-aminothiazol-4-yl)-2-(2-carboxyprop-2-oxyimino)acetamido]-3-[(E)-3-[(1-carbamoyl-1-propen-3-yl)-3-ethylmethylammonio]-1-propen-1-yl]3-cephem-4-carboxylate p-methoxybenzyl 7β-[(Z)-2-(2-carboxyprop-2-oxyimino)-2-(2-tritylaminothiazol-4-yl)acetamido]-3-[(Z)-3-chloro-1-propen-1-yl]3-cephem-4-carboxylate(1.5 g), sodium iodide (0.75 g) and 4-ethylmethylamino-2-butenylamide (0.28 g) were reacted in the same manner as described in Example 1 to obtain the target product(210 mg).

mp: 204° C.(dec.); IR(KBr, cm−1): 1760, 1663, 1610, 1530. NMR(DMSO-$d_6$) δ (ppm): 1.29(t,1H), 1.49(s,6H), 2.98(s,3H), 3.85(q,2H), 3.90(d,2H), 3.94(d,2H), 4.75(s,2H), 5.08(d,1H), 5.62(d,1H), 5.68(br d,1H), 6.75(d,1H), 6.99~7.12(br d,1H), 7.21~7.38(d,1H. s,1H), 9.59(d,1H).

EXAMPLE 10

Synthesis of 7β-[(Z)-2-(2-aminothiazol-4-yl)-2-(2-carboxyprop-2-oxyimino)acetamido]-3-[(E)-3-[(4-methylthiazol-5-yl)-methyldimethylammonio]-1-propen-1-yl]3-cephem-4-carboxylate p-methoxybenzyl 7β-[(Z)-2-(2-carboxyprop-2-oxyimino)-2-(2-tritylaminothiazol-4-yl)acetamido]-3-[(Z)-3-chloro-1-propen-1-yl]3-cephem-4-carboxylate(1.5 g), sodium iodide (0.75 g) and 5-dimethylam-inomethyl-4-methylthiazole(0.31 g) were reacted in the same manner as described in Example 1 to obtain the target product(180 mg).

mp: 198° C. (dec.); IR(KBR, cm−1): 1762, 1665, 1610, 1525. NMR(DMSO-$d_6$) δ (ppm): 1.50(s,6H), 2.43(s,3H), 2.91(s,6H), 3.41(s,2H), 4.03(d,2H), 4.60(d,2H), 4.60(s,2H), 5.05(d,1H), 5.57(d,1H), 5.65(br d,1H), 7.1~7.4(d,1H. s,1H. s,1H), 9.62(d,1H).

EXAMPLE 11

Synthesis of 7β-[(Z)-2-(2-aminothiazol-4-yl)-2-fluoroethoxyiminoacetamido]-3-[(E)-3-[(4-methylthiazol-5-yl)-methyldimethylammonio]-1-propen-1-yl]3-cephem-4-carboxylate p-methoxybenzyl 7β[(Z)-2-fluoroethoxyimino-2-(2-tritylaminothiazol-4-yl)acetamido]3-[(Z)-3-chloro-1-propen-1-yl]3-cephem-4-carboxylate (1.3 g), sodium iodide (0.68 g) and 5-dimethylaminomethyl-4-methylthiazole(0.27 g) were reacted in the same manner as described in Example 1 to obtain the target product (300 mg).

mp: 196° C.(dec.); IR(KBr,cm−1): 1765, 1665, 1610, 1530; NMR(DMSO-$d_6$) δ (ppm): 2.41(s,3H), 2.95(s,6H), 3.42(s,2H), 4.04(d,2H), 4.25(t,2H), 4.53(t,2H), 4.79(s,2H), 5.04(d,1H), 5.56(d,1H), 5.61(br d,1H), 7.1~7.4(d,1H. s,1H. s,1H), 9.65(d,1H).

EXAMPLE 12

Synthesis of 7β-[(Z)-2-(2-aminothiazol-4-yl)-2-fluoroethoxyiminoacetamdo]-3-[(E)-3-[(1-carbamoyl-1-propen-3-yl)-3-ethylmethylammonio]-1-propen-1-yl]3-cephem-4-carboxylate p-methoxybenzyl 7β-[(Z)-2-fluoroethoxyimino-2-(2-tritylaminothiazol-4-yl)acetamido]-3-[(Z)-3-chloro-1-propen-1-yl]3-cephem-4-carboxylate (1.3 g), sodium iodide (0.68 g) and 4-ethylmethylamino-2-butenylamnide (0.25 g) were reacted in the same manner as described in Example 1 to obtain the target product(230 mg).

mp: 191 ° C.(dec.); IR(KBr,cm−1): 1760, 1672, 1600, 1530; NMR(DMSO-$d_6$) δ (ppm): 1.27(t,1H), 2.99(s,3H), 3.85(q,2H), 3.90(d,2H), 3.94(d,2H), 4.27(t,2H), 4.52(t,2H), 4.75(s,2H), 5.09(d,1H), 5.60(d,1H), 5.69(br d,1H), 6.74(d, 1H), 7.19~7.35(d,1H. s,1H), 9.61(d,1H).

EXAMPLE 13

Synthesis of 7β-[(Z)-2-(5-amino-1,2,4-thiadiazol-3-yl)-2-methoxyiminoacetamido]-3-[(E)-3-[(1-carbamoyl-1-propen-3-yl)-3-ethylmethylammonio]-1-propen-1-yl]3-cephem-4-carboxylate To a solution of p-methoxybenzyl 7β[(Z)-2-(5-amino-1,2,4-thiadiazol-3-yl)-2-methoxyiminoacetamido]-3-[(Z)-3-chloro-1-propen-1-yl]3-cephem-4-carboxylate(1.5 g) dissolved in acetone(20 ml), sodium iodide (0.82 g) was added thereto under ice-cooling. The resulting solution was stirred for 15 minutes under ice-cooling and for additional an hour at room temperature. The solvent was distilled off, and the residue was extracted with ethyl acetate. The extract was washed with a 10%-sodium thiosulfate and with a saturated brine, followed by drying with addition of anhydrous magnesium sulfate. The dried extract was concentrated under reduced pressure and the resulting precipitates were collected by filtration to obtain 1.1 g of p-methoxybenzyl 7β-[(Z)-2-(5-amino-1,2,4-thiadiazol-3-yl)-2-methoxyiminoacetamido]-3-[(E)-3-iodo-1-propen-1-yl]3-cephem-4-carboxylate. The powder was dissolved in N,N-dimethylformamide(2.5 ml), and 4-ethylmethylamino-2-butenylamide(0.2 g) was added thereto at −10° C. The resulting solution was stirred for 4 hours at −10° C. 10%-sodium thiosulfate(70 ml) was added to the reaction solution, and the resulting precipitates were collected by filtration to obtain the yellowish brown powder. The powder was stirred in 88%-formic acid(1.3 ml) for 3 hours at room temperature, and acetone(400 ml) was added thereto. The resulting precipitates were collected by filtration and washed with acetone. The precipitates were chromatographed over silicagel[acetonitrile:distilled water 4:1 (v/v)], Sephadex LH-20(or Amberlite XAD-2), and then lyophilized to obtain the target product (180 mg) as white solid.

mp: 202° C.(dec.); IR(KBr,cm−1): 1765, 1670, 1600, 1520; NMR(DMSO-$d_6$) δ (ppm): 1.29(t,3H), 2.99(s,3H), 3.83(s,3H), 3.84(q,2H), 3.91(d,2H), 3.94(d,2H), 4.73(s,2H), 5.07(d,1H), 5.66(d,1H), 5.69(br d,1H), 6.59(dd,1H), 6.99~7.15(br d,1H), 7.28(dd, 1H), 8.63(d,1H), 9.59(d,1H).

EXAMPLE 14

Synthesis of 7β-[(Z)-2-(5-amino-1,2,4-thiadiazol-3-yl)-2-fluoroethoxyiminoacetamido]-3-[(E)-3-[(4-methylthiazol-5-yl)-methyldimethylammonio]-1-propen-1-yl]3-cephem-4-carboxylate p-methoxybenzyl 7β[(Z)-2-(5-amino-1,2,4-thiadiazol-3-yl)-2-fluoroethoxyiminoacetamido]-3-[(E)-3-iodo-1-propen-1-yl]3-cephem-4-carboxylate(1.1 g) and 5-dimethylaminomethyl-4-methylthiazol (0.36 g) were reacted in the same manner as discribed in Example 13 to obtain the target product(330 mg).

mp: 188° C.(dec.); IR(KBr,cm−1): 1763, 1670, 1595, 1522; NMR(DMSO-$d_6$) δ (ppm): 2.40(s,3H), 2.93(s,6H), 3.42(s,2H), 4.04(d,2H), 4.28(t,2H), 4.55(t,2H), 4.78(s,2H), 5.03(d,1H), 5.57(d,1H), 5.61(br d,1H), 7.1~7.32(d,1H. s,1H), 9.63(d,1H).

EXAMPLE 15

Synthesis of 7β-[(Z)-2-(5-amino-1,2,4-thiadiazol-3-yl)-2-fluoroethoxyiminoacetamido]-3-[(E)-3-[(1-carbamoyl-1-propen-3-yl)-3-ethylmethylammonio]-1-propen-1-yl]3-cephem-4-carboxylate p-methoxybenzyl 7β-[(Z)-2-(5-amino-1,2,4-thiadiazol-3-yl)-2-fluoroethoxyiminoacetamido]-3-[(E)-3-iodo-1-propen-1-yl]3-cephem-4-carboxylate(1 g) and 4-ethylmethylamino-2-butenylamide(0.3 g) were reacted in the same manner as described in Example 13 to obtain the target product(290 mg).

mp: 196° C.(dec.); IR(KBr,cm−1): 1762, 1680, 1600, 1520; NMR(DMSO-$d_6$) δ (ppm): 1.27(s,1H), 2.98(s,3H), 3.83(q,2H), 3.91(d,2H), 3.94(d,2H), 4.27(t,2H), 4.55(t,2H), 4.76(s,2H), 5.11(d,1H), 5.60(d,1H), 5.70(br d,1H), 6.75(d, 1H), 7.03~7.17(d,1H), 9.59(d, 1H).

EXAMPLE 16

Synthesis of 7β-[(Z)-2-(5-amino-1,2,4-thiadiazol-3-yl)-2-fluoroethoxyiminoacetamido]-3-[(E)-3-[(1-carbamoyl-1-propen-3-yl)-3-dimethylammonio]-1-propen-1-yl]3-cephem-4-carboxylate p-methoxybenzyl 7β-[(Z)-2-(5-amino-1,2,4-thiadiazol-3-yl)-2-fluoroethoxyiminoacetamido]-3-[(E)-3-iodo-1-propen-1-yl]3-cephem-4-carboxylate(1.2 g) and 4-dimethylamino-2-butenylamide(0.32 g) were reacted in the same manner as described in Example 13 to obtain the target product(230 mg).

mp: 184° C.(dec.); IR(KBr,cm$^{-1}$): 1762, 1675, 1598, 1520; NMR(DMSO-d$_6$) δ (ppm): 3.10(s,6H), 3.88(d,2H), 3.92(d,2H), 3.93(d,2H), 4.25(t,2H), 4.52(t,2H), 4.77(s,2H), 5.15(d,1H), 5.59(d,1H), 5.71(br d,1H), 6.72(d,1H), 7.01~7.22(br d,1H), 7.15~7.34(d,1H), 9.62(d,1H).

EXAMPLE 17

Synthesis of p-methoxybenzyl 7β-benzylideneamino-3-[(E)-3-[(1-carbamoyl-1-propen-3-yl)-3-ethylmethylammonio]-1-propen-1-yl]3-cephem-4-carboxylate iodide To a solution of p-methoxybenzyl 7β-benzylideneamino-3-[(Z)-3-chloro-1-propen-1-yl]3-cephem-4-carboxylate (1.6 g) dissolved in acetone(10 ml), sodium iodide(1.5 g) was added thereto under ice-cooling. The resulting solution was stirred for 3 hours at room temperature. The solvent was distilled off, and the residue was extracted with ethyl acetate. The extract was washed with a 10%-sodium thiosulfate and with a saturated brine, followed by drying with addition of anhydrous magnesium sulfate. The dried extract was concentrated to about 20 ml. To the concentrate was added 4-ethylmethyl-amino-2-butenylamide (0.57 g) in ethyl acetate(30 ml). The mixture was stirred for 2 hours at 0° C., and ethyl ether(50 ml) was added thereto. The resulting precipitates were collected by filtration to obtain the target product(1.5 g).

IR(KBr,cm$^{-1}$): 1762, 1678, 1600; NMR(DMSO-d$_6$) δ (ppm): 1.27(t,3H), 3.14(s,3H), 3.41~3.82(m,4H), 3.73(s, 3H), 3.95(br,2H), 4.26(m,2H), 5.23(d,1H), 5.44(d,1H), 5.74 (br d,1H), 6.17(m,1H), 6.79(d,1H), 7.01~7.19(br d,1H), 7.28(d,1H), 7.3~7.9(m,9H), 8.51(br s,1H).

EXAMPLE 18

Synthesis of 7β-amino-3-[(E)-3-[(1-carbamoyl-1-propen-3-yl)-3-ethylmethylammonio]-1-propen-1-yl] 3-cephem-4-carboxylate hydrochloride The compound(1.5 g) prepared in Example 17 was added 90%-formic acid(4.2 ml) and 35%-hydrochloric acid(0.85 ml). The resulting mixture was stirred for 90 minutes at room temperature, and acetone(500 ml) was added thereto. The resulting precipitates were collected by filtration to obtain the target product(0.6 g).

IR(KBr,cm$^{-1}$): 1786, 1688; NMR(DMSO-d$_6$) δ (ppm): 1.27(t,3H), 3.11(s,3H), 3.24~4.35(m,6H), 4.08(br,2H), 5.22 (br,2H), 6.0~6.5(m,1H), 7.04(d,1H), 7.27(d,1H), 7.36(m, 1H).

EXAMPLE 19

Synthesis of 7β-[(Z)-2-(5-amino-1,2,4-thiadiazol-3-yl)-2-fluoroethoxyiminoacetamido]-3-[(E)-3-[(1-carbamoyl-1-propen-3-yl)-3-ethylmethylammonio]-1-propen-1-yl]3-cephem-4-carboxylate The compound(0.6 g) prepared in Example 18 was added water:methyl alcohol(1:6, 26 ml), sodium acetate(0.61 g) and (Z)-2-(5-amino-1,2,4-thiadiazol-3-yl)-2-fluoroethoxyiminoaceticacidchloride hydrochloride (0.43 g). The resulting mixture was stirred for 3 hours at 25~30° C. After the mixture cooled to 0° C., insoluble materials were filtered off. The filtrate was chromatographed over silicagel[acetonitrile:distilled water 4:1(v/v)], Sephadex LH-20(or Amberlite XAD-2), and then lyophilized to obtain the target product(420 mg) as white solid.

mp, IR, NMR: Identical with Example 14

Experimental Tests 1. in vitro activity test

In order to illustrate the surprisingly superior antibacterial activity of the compounds of the present invention, the minimal inhibitory concentrations(MIC) of the compounds synthesized in the above Examples were determined and compared with Cefotaxime and Cefpirome which were used as the control compounds. These MIC values were determined by agar dilution method: that is, two-fold dilutions of each of the test compounds were made and dispersed in a Mueller-Hinton Broth medium. Standard test strain which had the 10$_6$ CFU per ml was inoculated on the medium, and was incubated at 37° C. for 18 to 20 hours. The results of the MIC tests are shown in Table 1.

TABLE 1

Minimal Inhibitory Concentration(MIC) of test compounds (μg/ml)

| Test Strain | Example 1 | Example 6 | Example 12 | CTX | CPR |
|---|---|---|---|---|---|
| 1. *Streptococcus pyogenes* 77A | 0.006 | 0.012 | 0.025 | 0.012 | 0.012 |
| 2. *Streptococcus faecium* MD 8b | 50 | 100> | 100> | 100> | 100 |
| 3. *Staphylococcus aureus* SG511 | 0.4 | 0.8 | 0.8 | 1.6 | 0.8 |
| 4. *Staphylococcus aureus* 285 | 0.4 | 0.4 | 0.8 | 1.6 | 0.4 |
| 5. *Staphylococcus aureus* 503 | 0.8 | 0.8 | 0.8 | 3.1 | 0.8 |
| 6. *Escherichia coli* 078 | <0.006 | 0.12 | 0.025 | 0.025 | 0.025 |
| 7. *Escherichia coli* DC 0 | 0.025 | <0.006 | <0.006 | 0.012 | 0.012 |
| 8. *Escherichia coli* DC 2 | 0.05 | 0.05 | 0.05 | 0.05 | 0.1 |
| 9. *Escherichia coli* TEM | 0.05 | 0.05 | 0.05 | 0.05 | 0.05 |
| 10. *Escherichia coli* 1507E | 0.025 | 0.05 | 0.05 | 0.025 | 0.025 |
| 11. *Pseudomonas aeruginosa* 9027 | 12.5 | 6.3 | 12.5 | 25 | 6.3 |
| 12. *Pseudomonas aeruginosa* 1592E | 3.1 | 3.1 | 6.3 | 25 | 3.1 |
| 13. *Pseudomonas aeruginosa* 1771 | 6.3 | 3.1 | 6.3 | 12.5 | 3.1 |
| 14. *Pseudomonas aeruginosa* 1771M | 0.4 | 0.4 | 0.8 | 0.4 | 0.8 |
| 15. *Salmonella typhimurium* | 0.1 | 0.1 | 0.4 | 0.1 | 0.1 |
| 16. *Klebsiella aerogenes* 1082E | 6.3 | 3.1 | 3.1 | 6.3 | 6.3 |

TABLE 1-continued

| Minimal Inhibitory Concentration(MIC) of test compounds ($\mu$g/ml) | | | | | |
|---|---|---|---|---|---|
| 17. *Klebsiella aerogenes* 1522E | 0.05 | 0.1 | 0.1 | 0.1 | 0.1 |
| 18. *Enterobacter cloace* P99 | 0.4 | 1.6 | 1.6 | 100> | 3.1 |
| 19. *Enterobacter cloace* 1321E | 0.012 | 0.025 | 0.05 | 0.05 | 0.025 |

| Test Strain | Example 13 | Example 14 | Example 15 | CTX | CPR |
|---|---|---|---|---|---|
| 1. *Streptococcus pyogenes* 71A | 0.025 | 0.05 | 0.025 | 0.012 | 0.012 |
| 2. *Streptococcus faecium* MD 8b | 100> | 100> | 100> | 100> | 100 |
| 3. *Staphylococcus aureus* SG511 | 0.8 | 0.4 | 0.8 | 1.6 | 0.8 |
| 4. *Staphylococcus aureus* 285 | 0.8 | 0.8 | 0.8 | 1.6 | 0.4 |
| 5. *Staphylococcus aureus* 503 | 0.8 | 0.8 | 0.8 | 3.1 | 0.8 |
| 6. *Escherichia coli* 078 | 0.05 | 0.012 | 0.025 | 0.025 | 0.025 |
| 7. *Escherichia coli* DC 0 | 0.025 | <0.006 | 0.012 | 0.012 | 0.012 |
| 8. *Escherichia coli* DC 2 | 0.2 | 0.05 | 0.1 | 0.05 | 0.1 |
| 9. *Escherichia coli* TEM | 0.05 | 0.025 | 0.05 | 0.05 | 0.05 |
| 10. *Escherichia coli* 1507E | 0.1 | 0.025 | 0.1 | 0.025 | 0.025 |
| 11. *Pseudomonas aeruginosa* 9071 | 3.1 | 12.5 | 3.1 | 25 | 6.3 |
| 12. *Pseudomonas aeruginosa* 1592E | 1.6 | 3.1 | 3.1 | 25 | 3.1 |
| 13. *Pseudomonas aeruginosa* 1771 | 1.6 | 3.1 | 3.1 | 12.5 | 3.1 |
| 14. *Pseudomonas aeruginosa* 1771M | 0.4 | 0.4 | 0.8 | 0.4 | 0.8 |
| 15. *Salmonella typhimurium* | 0.2 | 0.1 | 0.2 | 0.1 | 0.1 |
| 16. *Klebsiella aerogenes* 1082E | 3.1 | 3.1 | 3.1 | 6.3 | 6.3 |
| 17. *Klebsiella aerogenes* 1522E | 0.2 | 0.025 | 0.05 | 0.1 | 0.1 |
| 18. *Enterobacter cloace* P99 | 1.6 | 0.4 | 0.8 | 100> | 3.1 |
| 19. *Enterobacter cloace* 1321E | 0.05 | 0.012 | 0.05 | 0.05 | 0.025 |

※ CTX: Cefotaxime
※ CPR: Cefpirome

As can be seen from Table 1, the cephalosporin compounds of the present invention possess potent and broad antibacterial activities as compared with the known broad spectrum cephalosporin antibiotics, Cefotaxime and Cefpirome. More specifically, MICs of Example 1, 6, 12, and 14 against *Staphylococcus aureus, Escherichia coli* and *Pseudomonas aeruginosa* were superior to that of Cefotaxime and similar to that of Cefpirome. Also, MICs of Example 13 against *Pseudomonas aeruginosa* was superior to that of Cefpirome.

2. Acute toxicity studies

In order to illustrate usefulness of the compounds of the present invention, acute toxicity test of the compounds synthesized in the above Examples were carried out. Each dose of the compounds dissolved in saline and buffer solution (PH=7.0) was administered by intravenous or subcutaneous injection. Mortalities of the animals was recorded seven days latter. The results of the acute toxicity studies are shown in Table 2.

TABLE 2

| | $LD_{50}$ mg/kg | |
|---|---|---|
| Compound | i.v | s.c |
| Example 1 | >3000 | >4000 |
| Example 2 | >2000 | >3000 |
| Example 6 | >3000 | >3000 |
| Example 12 | >2000 | >3000 |
| Example 13 | >2000 | >3000 |
| Example 15 | >2000 | >3000 |

※ Mouse: Male ICR strain, 4 weeks

The compounds of the Example 1, 2, 6, 12, 13 and 15 are shown high stability as an antimicrobial medicament from >2000 mg/Kg in intravenous routes and >3000 mg/Kg in subcutaneous routes. Accordingly, the compounds of the present invention can be used in the therapeutic treatment of human beings or animals infected with variety of Gram-positive or Gram-negative bacteria.

The compounds of the present invention may be administered 1~3 times in an amount ranging from 50~5000 mg/day. The present invention also includes within its scope pharmaceutical compositions comprising one or more of the compound(I) and their derivatives as active ingredients, in association with pharmaceutically acceptable carriers, excipients or other additives, if necessary. The compositions may be formulated into various forms such as tablets, capsules, solution, injection, syrup, ointment, cream, suppositories, which may contain conventional additives such as a dispersant, suspending agent, stabilizer and the like.

Formulation examples are described below.

| Formulation example 1 | |
|---|---|
| The compound of prepared Example 1 | 100 mg |
| Lactose | 100 mg |
| Corn starch | 50 mg |
| Talc | 45 mg |
| Magnesium stearate | 5 mg |

The above compositions are formulated into tablets by the conventional tablets preparation method.

| Formulation example 2 | |
|---|---|
| The compound of prepared Example 6 | 100 mg |
| Lactose | 50 mg |
| Corn starch | 100 mg |
| Talc | 20 mg |
| Magnesium stearate | 5 mg |

The above compositions are formulated into capsules by the conventional capsules preparation method.

| Formulation example 3 | |
|---|---|
| The compound of prepared Example 13 | 250 mg |
| Sodium chloride | 12.5 mg |

The above compositions are formulated into injection by the conventional injection preparation method.

What is claimed is:

1. A compound of the following formula (I) or a pharmaceutically acceptable non-toxic salt thereof:

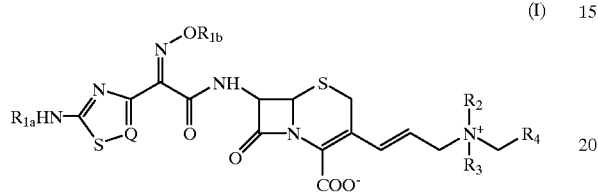
(I)

wherein $R_{1a}$ is a hydrogen atom;

$R_{1b}$ is a hydrogen atom, $C_{1-4}$ alkyl group or fluoro-substituted $C_{1-3}$ alkyl group;

Q is CH or N;

$R_2$ and $R_3$ may be the same or different and are individually a $C_{1-3}$ alkyl group; and $R_4$ is

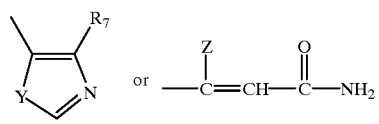

wherein $R_7$ is a $C_{1-3}$ alkyl group;
Y is O or S; and
Z is a hydrogen atom or $C_{1-3}$ alkyl group.

2. The compound of formula (I) or the pharmaceutically acceptable salt thereof recited in claim 1, wherein $R_{1a}$ is a hydrogen atom; $R_{1b}$ is a methyl group, ethyl group, fluoromethyl group or 2-fluoroethyl group;

$R_2$ and $R_3$ may be the same or different and are individually a methyl or ethyl group;

Q is CH or N; and $R_4$ is

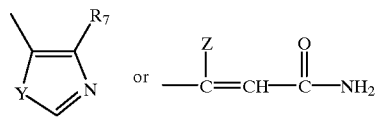

wherein $R_7$ is a methyl group;
Y is O or S; and
Z is a hydrogen.

3. A compound of the following formula (VIII):

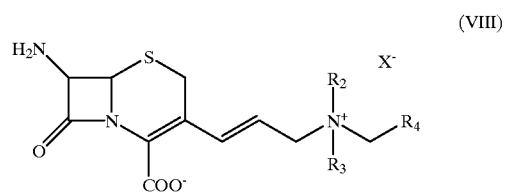
(VIII)

wherein $R_2$ and $R_3$ may be the same or different and are individually a $C_{1-3}$ alkyl group;

X is a halogen atom; and $R_4$ is

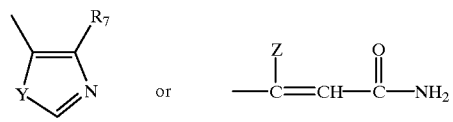

wherein $R_7$ is a $C_{1-3}$ alkyl group;
Y is O or S; and
Z is a hydrogen atom or $C_{1-3}$ alkyl group.

4. A pharmaceutical composition comprising a therapeutically effective amount of the cephalosporin compound (I) or the pharmaceutically acceptable non-toxic salt thereof:

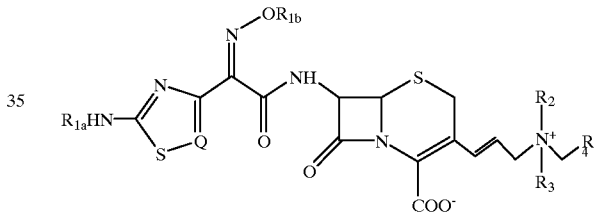
(I)

wherein $R_{1a}$ is a hydrogen atom;

$R_{1b}$ is a hydrogen atom, $C_{1-4}$ alkyl group or fluoro-substituted $C_{1-3}$ alkyl group;

Q is CH or N;

$R_2$ and $R_3$ may be the same or different and are individually a $C_{1-3}$ alkyl group; and $R_4$ is

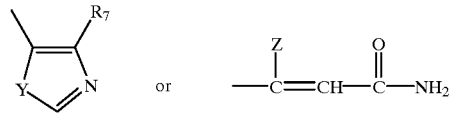

wherein
$R_7$ is a $C_{1-3}$ alkyl group;
Y is O or S; and
Z is a hydrogen atom or $C_{1-3}$ alkyl group.

* * * * *